(12) United States Patent
Sircar et al.

(10) Patent No.: US 6,709,846 B1
(45) Date of Patent: Mar. 23, 2004

(54) METHODS OF PRODUCING ESTERS OF MYCOPHENOLATE

(75) Inventors: Anindya Sircar, Calcutta (IN); Anand Khedkar, Mumbai (IN); Madhay Kulkarni, Vaduj (IN); Shrikumar Suryanarayan, Bangalore (IN); Madhavan Sridharan, Bangalore (IN); Poornaprajna Acharya, Bangalore (IN); Ganesh Samvasivam, Bangalore (IN); Ramakrishnan Melarkode, Bangalore (IN)

(73) Assignee: Biocon India Limited, Bangalore (IN)

( * ) Notice: Subject to any disclaimer, the term of this patent is extended or adjusted under 35 U.S.C. 154(b) by 0 days.

(21) Appl. No.: 09/857,579

(22) PCT Filed: Dec. 9, 1999

(86) PCT No.: PCT/IN99/00070

§ 371 (c)(1),
(2), (4) Date: Jun. 7, 2001

(87) PCT Pub. No.: WO00/34503

PCT Pub. Date: Jun. 15, 2000

(30) Foreign Application Priority Data

Dec. 9, 1998 (IN) .................................. 2754/MAS/98

(51) Int. Cl.$^7$ .................. C12P 17/16; C07D 413/12
(52) U.S. Cl. ........................................ 435/118; 544/153
(58) Field of Search .......................... 435/118; 544/153

(56) References Cited

U.S. PATENT DOCUMENTS

| | | | |
|---|---|---|---|
| 4,753,935 A | 6/1988 | Nelson et al. | ........... 514/233.5 |
| 5,247,083 A | 9/1993 | Knox et al. | ................. 544/153 |

FOREIGN PATENT DOCUMENTS

| WO | WO 95/07902 | 3/1995 |
|---|---|---|

*Primary Examiner*—Bruck Kifle
*Assistant Examiner*—Thomas McKenzie
(74) *Attorney, Agent, or Firm*—Sidley Austin Brown Wood LLP

(57) ABSTRACT

Methods for the manufacture of Mycophenolate are disclosed. Mycophenblate mofetil is biochemically synthesized using Mycophenolic Acid and 2-morpholino ethanol with the help of an enzyme. Mycophenolate mofetil is also chemically synthesized non-catalytically by refluxing mycophenolic acid with 2-morpholino ethanol in the absence of a third solvent or a catalyst.

20 Claims, No Drawings

METHODS OF PRODUCING ESTERS OF MYCOPHENOLATE

This invention relates to an improved process for the manufacture of Mycophenolate Mofetil by a biochemical method using enzymes or chemically without the use of any catalyst

BACKGROUND

Mycophenolate mofetil of formula I is the morpholinoethyl ester of Mycophenolic acid (MPA).

Formula I

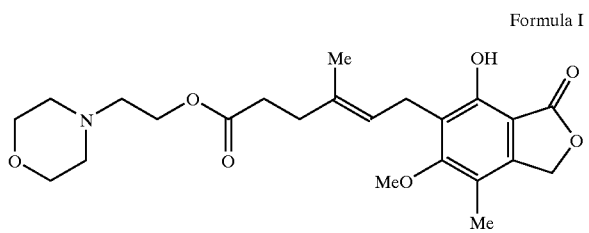

Mycophenolate mofetil is an immunosuppressant. It is derived from mycophenolic acid which was isolated from a fungus and chemically modified to improve oral absorption. Mycophenolate mofetil, the pharmaceutically acceptable salt thereof is used as an immunosuppressive agent, antiinflammatory, anti-tumor and anti-viral agent.

Chemical synthesis route for the manufacture of Mycophenolate mofetil already exists. An acid halide condensation route for the synthesizing the Mycophenolate mofetil has been described in U.S. Pat No. 4,753,935; which requires two steps and has a high dimeric impurity(2%) among others requiring additional recrystallization step. Those skilled in the field of esterification reactions will appreciate that the conventional teachings for the synthesis of an ester through the reaction of an acid and an alcohol require the use of a chemical catalyst to achieve acceptable yields. Furthermore, catalytic reaction entail the added cost of the catalyst and the additional steps of its addition and separation from the reaction mixture. The direct esterification of mycophenolic acid without any catalyst too has been disclosed in U.S. Pat. No. 5,247,083, in which the reaction is carried out in the presence of an inert organic solvent.

It has surprisingly been discovered that good yields of mycophenolate mofetil can be obtained without the disadvantage of prior described methods, without the use of a third organic solvent and without the use of chemical catalysts. It has also been found that it is possible to produce mycophenolate mofetil under very mild conditions using enzymes, in the presence of water and organic solvents and no other chemical catalysts. These processes reduce the chances of unwanted side reaction and lead to purer products.

SUMMARY OF THE INVENTION

The present invention concerns methods for making Mycophenolate mofetil by:
(i) reacting the Mycophenoiic acid and a molar excess of 2-morpholino ethanol in an organic solvent along with an enzyme and an appropriate quantity of water.
(ii) refluxing Mycophenolic acid with a large excess of 2-morpholino ethanol in the absence of any other organic solvent or a catalyst.

DETAILED DESCRIPTION OF THE INVENTION

This invention relates to a process for the conversion of Mycophenolic acid and 2-morpholino ethanol into Mycophenolate Mofetil.

According to one method of this invention the substrates, MPA and 2-morpholino ethanol are added in an organic solvent or a mixture of more than one organic solvents water is added to the system to adjust the water content and pH in the microenvironment, enzyme is added to this system, the mixture is incubated at a temperature between 20 to 55 deg C., the reaction is carried out for a time upto 120 hr, the esterified product is analyzed by HPLC method.

The MPA is used in a concentration range of 0.03 to 5%. The 2-morpliolino ethanol is used in molar equivalent of 1 to 15 with respect to MPA. The MPA and 2-morpholino ethanol are added to the organic solvent or mixture of organic solvents more than one, where the organic solvent is a C6–C12 alkane such as iso-octane, n-hexane, cyclohexane, heptane, octane or a C2–C12 alcohol such as ethanol, propanol, 2-propanol, hexanol, octanol, or isopropanol. A surfactant is added to the organic solvent or in the mixture of the organic solvents which is Sodium bis (ethylhexyl) sulfosuccinate (Aerosol OT or AOT), Cetyl trimethyl ammonium bromide or Trimethyl octyl ammonium chloride (TOMAC). The water content (Wo), which is the molar ratio of the water to the surfactant, is adjusted to a value in the range of 1 to 30. The pH of the microenvironment is adjusted in a range of 3 to 8 using buffer such as acetate or phosphate buffer. The enzyme, which is used for the bioconversion is a hydrolase which may be lipase cutinase, esterase or a protease from microbial, animal or plant origin. The enzyme is added in organic solvent in absence or presence of a surfactant. The reaction is carried out at a temperature in a range of 20 to 55 deg C. The time period of reaction is upto 120 hrs. The esterified product is analyzed by HPLC method.

Another method for producing mycophenolate mofetil comprises heating and or refluxing MPA (mycophenolic acid) with a large excess of 2-morpholino ethanol in the absence of any other organic solvent or catalyst. The MPA is heated and optionally refluxed with a large excess of 2-morphoiino ethanol at a temperature between 80 to 150 deg C. The reaction is carried out for a time period of 6 to 120 hrs.

Both of these methods are illustrated with examples below which are not intended to be limiting.

EXAMPLE 1

A 50 mM solution of AOT in 10 ml isooctane was prepared. In the surfactant solution MPA in a concentration of 0.6 mM and 2-morpholino ethanol 0.9 mM were added. To this mixture acetate buffer (pH 5.0) was added to adjust the Wo to 3.0. Lipase from *Candida rugosa* was added in a concentration of 1 mg/ml. The reaction mixture was incubated at a temperature of 37 deg C. for 24 hrs. The esterified product was analyzed by HPLC.

EXAMPLE 2

A 100 mM solution of AOT in 10 ml isooctane was prepared. In the suractant solution MPA in a concentration of 0.6 mM and 2-morpholino ethanol 9.0 mM were added. To this mixture acetate buffer (pH 4.5) was added to adjust the Wo to 2.8. Lipase from *Mucor meihei* was added in a concentration of 10 mg/ml. The reaction mixture was incubated at a temperature of 37 deg C. for 48 hrs. The esterified product was analyzed by HPLC.

EXAMPLE 3

A 100 mM solution of AOT in 50 ml isooctane was prepared. In the surfactant solution MPA in a concentration of 0.6 mM and 2-morpholino ethanol 9.0 mM were added. To this mixture acetate buffer (pH 4.5) was added to adjust the Wo to 10. Lipase from *Candida albicans* was added in a concentration of 7 mg/ml. The reaction mixture was incubated at a temperature of 37 deg C. for 48 hrs. The esterified product was analyzed by HPLC.

EXAMPLE 4

A 100 mM solution of CTAB in 50 ml isooctane with ethanol as a cosolvent was prepared. In the surfactant solution MPA in a concentration of 0.6 mM and 2-morpholino ethanol 9.0 mM were added. To this mixture phosphate buffer (pH 7.0) was added to adjust the Wo to 20. Pig liver esterase was added in a concentration of 5 mg/ml. The reaction mixture was incubated at a temperature of 37 deg C. for 96 hrs. The esterified product was analyzed by HPLC.

EXAMPLE 5

A 100 mM solution of TOMAC in 50 ml octanol with propanol as a cosolvent was prepared. In the surfactant solution MPA in a concentration of 0.6 mM and 2-morpholino ethanol 9.0 mM were added. To this mixture acetate buffer (pH 4.5) was added to adjust the Wo to 2.8. Protease from serratia marcesens was added in a concentration of 7 mg/ml. The reaction mixture was incubated at a temperature of 45 deg C. for 120 hrs. The esterified product was analyzed by HPLC.

EXAMPLE 6

A microemulsion system using hexane, water and 2 propanol in mole fraction ratio of 0.23:0.32:0.45 was prepared. In the solution MPA in a concentration of 0.6 mM and 2-morpholino ethanol 9.0 mM were added. Protease from *Bacillus subtilis* was added in a concentration of 7 mg/ml. Cutinase was added in a concentration of 7 mg/ml. The reaction mixture was incubated at a temperature of 37 deg C. for 48 hrs. The esterified product was analyzed by HPLC.

EXAMPLE 7

A 150 mM solution of AOT in 100 ml isooctane was added. In the surfactant solution MPA in a concentration of 0.6 mM and 2-morpholino ethanol 9.0 mM were added. To this mixture acetate buffer (pH 4.5) was added to adjust the Wo to 1.5. Lipase from Mucor meihei was added in a concentration of 5 mg/ml. The reaction mixture was incubated at a temperature of 20 deg C. for 48 hrs. The esterified product was analyzed by HPLC.

EXAMPLE 8

10 mg of MPA was taken in 10 mL of 2-morpholino ethanol and the mixture was heated to 100 deg C. The temperature was maintained between 140 to 150 deg C. for about 6 hrs. After the reaction was complete, 100 mL of ethyl acetate was added, the organic layers were washed with 3×100 mL of water, dried over $Na_2SO_4$ and the ethyl acetate was removed under reduced pressure to afford the product.

EXAMPLE 9

10 mg of MPA was taken in 10 mL of 2-morpholino ethanol and the mixture was heated to 140 deg C. under reflux. The temperature was maintained between 140 to 150 deg C. for about 6 hrs. After the reaction was complete, 100 mL of ethyl acetate was added, the organic layers were washed with 3×100 mL of water, dried over $Na_2SO_4$ and the ethyl acetate was removed under reduced pressure to afford the product, mycophenolate mofetil.

EXAMPLE b 10

12.5 mg of MPA was taken in 20 mL of 2-morpholino ethanol and the mixture was heated to 80 deg C. The temperature was maintained between 80 to 85 deg C. for about 96 hrs. After the reaction was complete, 100 mL of ethyl acetate was added, the organic layers were washed with 3×100 ml of water, dried over $Na_2SO_4$ and the ethyl acetate was removed under reduced pressure to afford the product.

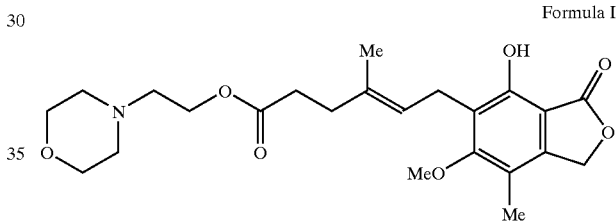

Formula I

We claim:

1. A method for the production of mycophenolate mofetil which comprises incubating mycophenolic acid with an excess of 2-morpholinoethanol at a temperature of 20° C. to 55° C. in the presence of an enzyme catalyst.

2. The method as claimed in claim 1, wherein the reaction is carried out for a time period of 6 to 120 hours.

3. The method as claimed in claim 1 wherein said enzyme catalyst is a hydrolase selected from the group consisting of a lipase, a cutinase, an esterase and a protease.

4. The method as claimed in claim 1 wherein said enzyme catalyst is a lipase or an esterase.

5. The method as claimed in claim 1 wherein said enzyme catalyst is in an immobilized form.

6. The method as claimed in claim 1 wherein said enzyme catalyst is in a non-immobilized form.

7. The method as claimed in claim 1 wherein said reaction is carried out in the presence of a surfactant.

8. The method as claimed in claim 7 wherein said surfactant is Sodium bis(2-ethylhexyl) sulfosuccinate, Cetyl trimethyl ammonium bromide or trimethyloctyl ammonium chloride.

9. The method as claimed in claim 1 wherein said enzyme is of microbial, animal or plant origin.

10. The method as claimed in claim 1 wherein the reaction is carried out in the presence of water.

11. The method as claimed in claim 10 wherein the water content (Wo) of the system is 1 to 30.

12. The method as claimed in claim 11 wherein the water content is 2 to 10.

13. The method as claimed in claim 10 wherein the pH of the water is 3 to 8.

14. The method as claimed in claim 13 wherein the pH of the reaction microenvironment is adjusted using an acetate buffer or a phosphate buffer.

15. The method as claimed in claim 1 wherein the reaction is carried out in the presence of an organic solvent.

16. The method as claimed in claim 15 wherein the organic solvent comprises one or more $C_6$–$C_{12}$ alkanes, one or more $C_6$–$C_{12}$ alcohols, or a mixture of two or more of these.

17. The method as claimed in claim 16 wherein said one or more alkanes are selected from the group consisting of iso-octane, n-hexane, cyclohexane, heptane and octane, and said one or more alcohols are selected from the group consisting of ethanol, propanol, isopropanol, hexanol and octanol.

18. A method for the production of mycophenolate mofetil which comprises heating mycophenolic acid with an excess of 2-morpholinoethanol at a temperature between 80° C. and 150° C. in the absence of any other organic solvent or catalyst.

19. The method as claimed in claim 18 wherein the reaction mixture is refluxed.

20. The method as claimed in claim 18, wherein the reaction is carried out for a time period of 6 to 120 hours.

* * * * *